(12) United States Patent
Steger et al.

(10) Patent No.: US 6,911,022 B2
(45) Date of Patent: Jun. 28, 2005

(54) SANITARY NAPKIN HAVING A WIPE ARTICLE ASSOCIATED THEREWITH

(75) Inventors: Christine Gail Steger, West Chester, OH (US); Dennis Allen Darby, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 133 days.

(21) Appl. No.: 09/839,741

(22) Filed: Apr. 20, 2001

(65) Prior Publication Data

US 2002/0156448 A1 Oct. 24, 2002

(51) Int. Cl.[7] ............................ A61F 13/15; A61F 13/20
(52) U.S. Cl. .......................... 604/385.05; 604/385.04; 604/385.06; 604/385.201; 604/387
(58) Field of Search .................. 604/385.01–385.06, 604/385.14, 385.13, 385.22, 385.24–387, 389–396, FOR 103, FOR 101

(56) References Cited

U.S. PATENT DOCUMENTS

| | | | |
|---|---|---|---|
| 4,191,609 A | | 3/1980 | Trokhan |
| 4,221,221 A | * | 9/1980 | Ehrlich .................. 604/585.06 |
| 4,342,314 A | | 8/1982 | Radel et al. |
| 4,463,045 A | | 7/1984 | Ahr et al. |
| 4,481,243 A | | 11/1984 | Allen |
| 4,556,146 A | | 12/1985 | Swanson et al. |
| 4,589,876 A | | 5/1986 | Van Tillburg |
| 4,687,478 A | | 8/1987 | Van Tillburg |
| 4,701,178 A | | 10/1987 | Glaug et al. |
| 4,702,378 A | * | 10/1987 | Finkel et al. .......... 604/385.06 |
| RE32,649 E | | 4/1988 | Brandt et al. |
| 4,753,647 A | * | 6/1988 | Curtis .................. 604/385.06 |
| 4,755,421 A | | 7/1988 | Manning et al. |
| 4,759,754 A | | 7/1988 | Korpman |
| 4,808,175 A | * | 2/1989 | Hansen .................. 604/385.06 |
| 4,848,572 A | | 7/1989 | Herrea |
| 4,917,693 A | * | 4/1990 | Terry .................... 604/385.06 |
| 5,111,934 A | * | 5/1992 | Morin |
| 5,241,710 A | | 9/1993 | Lockhart |
| 5,350,067 A | | 9/1994 | Beltran |
| 5,462,166 A | | 10/1995 | Minton et al. |
| 5,569,230 A | | 10/1996 | Fisher et al. |
| 5,595,807 A | | 1/1997 | Gooding, Jr. et al. |
| 5,662,639 A | * | 9/1997 | Tanaka et al. ............. 604/396 |
| 5,662,758 A | | 9/1997 | Hamilton et al. |
| 5,702,379 A | * | 12/1997 | Preiss .................... 604/385.13 |
| 5,800,654 A | | 9/1998 | Davis et al. |
| 6,074,376 A | | 6/2000 | Mills |
| 6,099,940 A | | 8/2000 | Hamilton et al. |

FOREIGN PATENT DOCUMENTS

| | | | | |
|---|---|---|---|---|
| WO | 9309743 | * | 5/1993 | ................ 604/389 |

* cited by examiner

*Primary Examiner*—Karin Reichle
(74) *Attorney, Agent, or Firm*—Matthew P. Fitzpatrick; Kevin C. Johnson; Roddy M. Bullock

(57) ABSTRACT

An absorbent article, preferably a sanitary napkin, having a body-facing side, a garment-facing side, a length, a width, and two longitudinal side margins. The sanitary napkin has a liquid pervious topsheet, a liquid impervious backsheet joined to the topsheet, and an absorbent core positioned between the topsheet and the backsheet. A pair of flaps are provided, each flap extending from a longitudinal side margin and each of the flaps are folded over the topsheet in a topsheet facing relationship. The flaps are maintained in the topsheet facing relationship by an enclosed pouch having a wipe article disposed therein. In a preferred embodiment the wipe article is a wet wipe. In a further embodiment, the absorbent article is an individually packaged sanitary napkin having a releasable wrapper affixed to the backsheet adhesive, and provided in a tri-folded package.

10 Claims, 6 Drawing Sheets

SANITARY NAPKIN HAVING A WIPE ARTICLE ASSOCIATED THEREWITH

FIELD OF THE INVENTION

This invention is directed to sanitary napkins, and particularly to sanitary napkins having flaps. More particularly, this invention is directed to the packaging of such sanitary napkins having a wipe article associated therewith.

BACKGROUND OF THE INVENTION

Sanitary napkins having flaps extending outwardly from the longitudinal side margins are well known in the art. For example, U.S. Pat. No. 4,589,876 issued May 20, 1986, to Van Tilburg and U.S. Pat. No. 4,687,478 issued Aug. 18, 1987, to Van Tilburg disclose preferred sanitary napkins with flaps and are incorporated herein by reference to illustrate particularly preferred flapped sanitary napkin constructions.

To conserve space during packaging, i.e., the period between manufacture of the sanitary napkin and its intended first use by the wearer, the flaps of such sanitary napkins are typically folded to overlay the backsheet. At the time of the first use by the wearer, the flaps are usually unfolded to facilitate installation of the sanitary napkin into the wearer's undergarment. Typically adhesive, interposed between the backsheet and the flap adhesive release paper, is used for maintaining the flaps in the folded disposition prior to the wearer's first use of the sanitary napkin.

Several attempts have been made to provide alternative means for maintaining the flaps in the desired disposition prior to first use of the sanitary napkin by the wearer. For example, U.S. Pat. No. 4,759,754 issued Jul. 26, 1988, to Korpman discloses an adhesive tab which can be used for maintaining the flaps in the desired disposition overlaying the backsheet during packaging. U.S. Pat. No. 4,701,178 issued Oct. 20, 1987, to Glaug et al. discloses a sanitary napkin having a single release strip which covers the centrally located adhesive of the backsheet and over which release strip the flaps are folded.

One successful alternative to maintaining the flaps in the desired position prior to first use is shown in U.S. Pat. No. 5,800,654 issued Sep. 1, 1998 to Davis et al., which is hereby incorporated herein by reference. Davis et al. teaches a sanitary napkin packaged with flaps folded over to the topsheet and a unitary release strip bridging the adhesive of the flaps. As such, the user can first place the sanitary napkin in the crotch area of her undergarment by use of a central adhesive provided. She then simply peels off the unitary release strip bridging the folded flaps and folds the flaps back and around the edges of the crotch of her undergarment.

Not only does the Davis et al. packaging configuration maintain the flaps in the desired position prior to use, it also maintains the clean, sanitary condition and appearance of the sanitary napkin's body contacting sheet. This is important because the user is typically concerned with such cleanliness. This concern for cleanliness extends to more than just the sanitary napkin itself. The user of such a sanitary napkin often finds it necessary or desirable to clean the area of the anatomy associated with the wearing of a sanitary napkin. For example, when changing a sanitary napkin, the user may wish to wipe the vaginal area with a suitable cleaning implement, such as a cloth, or a wipe article such as a disposable towelette.

Several attempts have been made at providing a disposable wipe with a sanitary napkin. For example, U.S. Pat. No. 5,569,230 issued Oct. 29, 1996 to Fisher et al., which is hereby incorporated by reference herein, discloses an individually packaged sanitary napkin having a cleansing wipe packaged therewith. The wipe can be packaged in flaps located on various different portions of the wrapper. However, this configuration has certain drawbacks when the sanitary napkin is not configured for individual packaging. Also, the cost of providing such extra wrapper material, as well as the associated processing can be prohibitive for commercially viable products.

Other attempts have been made at providing a prewrapped moistened towelette with a sanitary napkin. For example, U.S. Pat. No. 4,848,572 issued Jul. 18, 1989 to Herrera teaches a towelette hermetically sealed in an elongate sheath releasably attached to an impermeable member of the sanitary napkin. However, the configuration shown requires the addition of significant material and components be added to the sanitary napkin. Also, the user must remove and use the wipe prior to placing the sanitary napkin for use in her undergarment, thereby causing inconvenience, and making the entire process rather awkward at a time when both ease of use and discreteness are appreciated.

Because of the sensitive nature of changing sanitary napkins, often under less than ideal circumstances, such as in public restrooms, it is desirable to provide a wipe for use with a sanitary napkin that is simple and convenient to use.

Furthermore, it is desirable to provide the wipe for use with a sanitary napkin in a commercially viable manner, that is, in a manner that does not cause the product to be cost prohibitive to market.

Additionally, it is desirable to provide a sanitary napkin having a flap disposition which promotes the cleanliness of the topsheet of the sanitary napkin during packaging and handling by the wearer prior to the first use of the sanitary napkin, and provides means for the user to conveniently and easily use a wipe article, if desired.

Finally, it is desirable to provide a convenient means for manipulating the flaps from the packaged arrangement to the disposition which the flaps will be used during wear, and to be provided with a vaginal wipe, which does not inconvenience the user by introducing additional time-consuming steps.

BRIEF SUMMARY OF THE INVENTION

An absorbent article is disclosed. The absorbent article is preferably a sanitary napkin having a body-facing side, a garment-facing side, a length, a width, and two longitudinal side margins. The sanitary napkin comprises a liquid pervious topsheet, a liquid impervious backsheet joined to said topsheet, and an absorbent core positioned between the topsheet and said backsheet. A pair of flaps are provided, each flap extending from a longitudinal side margin and each of the flaps are folded over the topsheet in a topsheet facing relationship. Means for maintaining the flaps in the topsheet facing relationship have a wipe article associated therewith. In a preferred embodiment the means for maintaining the flaps in the topsheet facing relationship comprises a release strip and the wipe article comprises a wet wipe. In a further embodiment, the absorbent article is an individually packaged sanitary napkin having a releasable wrapper affixed to the backsheet adhesive, and provided in a tri-folded package.

BRIEF DESCRIPTION OF THE DRAWINGS

While the Specification concludes with claims particularly pointing out and distinctly claiming the present in-vention, it is believed the invention will be better understood from the following description taken in conjunction with the accompanying drawings wherein like parts are given the same reference numeral, analogous parts are designated with a prime symbol, related parts are designated by alphabetic characters, adhesive is shown in phantom and:

DETAILED DESCRIPTION OF THE INVENTION

Figure 1:
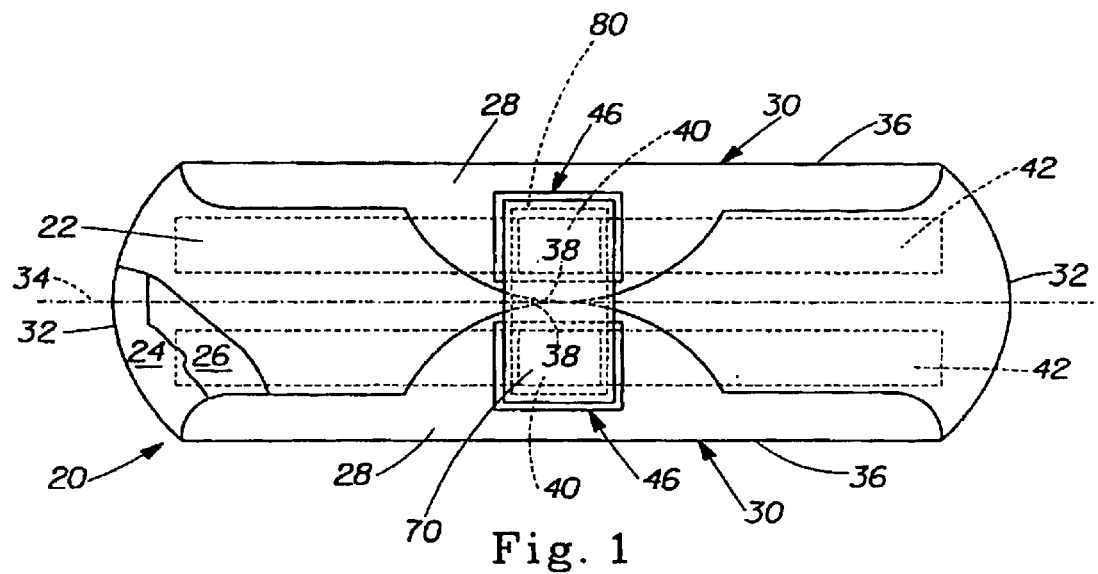
FIG. 1 is a top plan view, shown partially in cutaway, of a sanitary napkin according to the present invention.

As shown in FIG. 1, the invention comprises a disposable absorbent article, particularly a sanitary napkin 20. The sanitary napkin 20 is used to collect vaginal discharges, such as menses, and prevent soiling of the wearer's clothing by such discharges. The sanitary napkin 20 features a liquid pervious topsheet 22, a liquid impervious backsheet 24, an absorbent core 26 intermediate the topsheet 22 and the backsheet 24 and at least one flap 28 extending from a longitudinal side margin 30 of the sanitary napkin 20, and preferably two symmetrically opposite flaps 28, one extending from each longitudinal side margin 30 of the sanitary napkin 20. The perimeter of the sanitary napkin 20 is defined by two longitudinal side margins 30 and two lateral side margins 32.

Associated with the sanitary napkin 20 is a means, such as adhesive, for releasably affixing the sanitary napkin 20 to the undergarment of a wearer. Adhesives such as pressure sensitive adhesives are suitable for this purpose. Numerous other equivalent means may also be used. For example adhesives which are not pressure sensitive adhesives, hook-type fasteners such as VELCRO, selectively activated attachment materials such as those described in U.S. Pat. Nos. 5,662,758 and 6,099,940 are also suitable. Because adhesives are most commonly used as the attachment means for currently marketed sanitary napkins, the attachment means will be described in terms of adhesive. It will be recognized by those of skill in the art, however, that this is not the only such means and that numerous equivalent attachment means are possible.

Each flap 28 may also have its own adhesive patch 40. Preferentially, such adhesive 40 is associated with the face of the flap 28 which contacts the undergarment of the wearer. That is, each flap has a garment contacting face or portion that contacts the wearer's undergarments in use. As will be understood from the description herein, the garment contacting face of the flap 28 is the portion that contacts the outside of the wearer's undergarment when in an in-use folded condition. Also the central portion of the sanitary napkin 20 intermediate the flaps 28 may have adhesive 42 associated with the area of the central portion of the sanitary napkin 20 which contacts the undergarment of the wearer. Preferentially such adhesive 42 is joined to the outwardly oriented face of the backsheet 24.

The sanitary napkin 20 has a longitudinal centerline 34 which conceptually divides the sanitary napkin 20 into two substantially symmetrically opposite halves. As used herein the term "longitudinal" refers to an imaginary line, axis or direction of the sanitary napkin 20, which line, axis or direction is typically centered between the longitudinal side margins 30 of the napkin and is generally aligned with the vertical plane which bisects a standing wearer into left and right body halves. The term "lateral" refers to an imaginary line, axis or direction generally orthogonal the longitudinal direction, within the plane of the sanitary napkin 20, and is generally sideways aligned relative to the wearer.

Examining the components in more detail with continuing reference to FIG. 1, the topsheet 22 is the component of the garment which is oriented towards and contacts the body of the wearer, and receives bodily discharges. The topsheet 22 is liquid pervious and should be flexible and nonirritating to the skin. As used herein the term "flexible" refers to materials which are compliant and readily conform to the shape of the body or respond by easily deforming in the presence of external forces. Preferably the topsheet 22 is not noisy, to provide discretion for the wearer. The topsheet 22 should be sanitary, clean in appearance and somewhat opaque to hide the bodily discharges collected in and absorbed by the core 26.

The topsheet 22 should further exhibit good strikethrough and rewet characteristics, permitting bodily discharges to rapidly penetrate the topsheet 22 to the core 26, but not flow back through the topsheet 22 to the skin of the wearer. Suitable topsheets 22 may be made from nonwoven materials or perforated polyolefinic films. The topsheet 22 has a plurality of apertures to permit liquids deposited thereon to pass through to the core 26. Such apertures may, but need not, be present in the flaps 28. An apertured polyolefinic film topsheet 22 having about 5 to about 60 percent open area, typically about 25 percent open area, and a thickness of about 0.01 to about 0.05 millimeters prior to aperturing and about 0.46 to about 0.51 millimeters after aperturing is suitable.

If desired, the topsheet 22 may be sprayed with a surfactant to enhance fluid penetration to the core 26. The surfactant is typically nonionic and should be nonirritating to the skin. A surfactant density of about 0.01 milligrams per square centimeter of topsheet 22 areas is suit-able. A suitable surfactant is sold by the Glyco Chemical, Inc. of Greenwich, Conn. as Pegosperse 200 ML.

A particularly suitable topsheet 22 may be made in accordance with U.S. Pat. No. 4,342,314 issued Aug. 3, 1982 to Radel et al. and U.S. Pat. No. 4,463,045 issued Jul. 31, 1984 to Ahr et al., which patents are incorporated herein by reference for the purpose of disclosing particularly preferred executions of liquid pervious topsheets. A topsheet 22 made of model X-3265 or model P1552 apertured formed film sold by the Tredegar, of Terre Haute, Ind. has been found to work well.

The backsheet 24 may be any flexible, liquid resistant, preferably liquid impervious material, such as a polyolefinic film. The backsheet 24 prevents discharges collected by and contained in the sanitary napkin 20, and particularly discharges absorbed by the core 26, from escaping the sanitary napkin 20 and soiling the clothing and bedding of the wearer. Preferably the backsheet 24 is not noisy, to provide discretion for the wearer.

The backsheet 24 may also be impervious to malodorous gases generated by absorbed bodily discharges, so that the malodors do not escape and become noticed by the wearer. A low density polyethylene backsheet 24 about 0.01 to about 0.05 millimeters in thickness, preferably about 0.02 millimeters in thickness, has been found to work well. A polyethylene film, such as is sold by Tredegar, under model XP-39385 has been found particularly well suited for the backsheet 24. The backsheet 24 may also permit gases or vapors to pass through it (i.e. be breathable) while still resisting the passage of liquids therethrough.

Further, the backsheet 24 may be made of a soft cloth-like material which is hydrophobic relative to the topsheet 22, e.g., a polyester or polyolefinic fiber backsheet 24 works well. A particularly preferred soft, clothlike backsheet 24 material is a laminate of a polyester non-woven material lamina and a film such as described in U.S. Pat. No. 4,476,180 issued to Wnuk.

In a particularly preferred embodiment, the backsheet 24 is slightly larger than the topsheet 22 and the intermediate absorbent core 26. In such an embodiment, the top-sheet 22 and intermediate absorbent core 26 are peripherally circumscribed by the backsheet 24 which has a radial margin of about 0.5 centimeters to about 1.5 centimeters, preferably about 1.0 centimeter, from the side margins of the topsheet 22. This geometry provides a marginal area of protection should the core 26 become overloaded or the sanitary napkin 20 otherwise fail. In such an embodiment the backsheet 24 and flaps 28 are preferably unitary and coextensive. The topsheet 22 and the backsheet 24 are preferentially peripherally joined using known techniques, either entirely so that the entire perimeter of the sanitary napkin 20 is circumscribed by such joinder or are partially peripherally joined at the perimeter. The term "joined" refers to the condition where a first member or component is affixed, or connected, to a second member or component either directly; or indirectly, where the first member or component is affixed, or connected, to an intermediate member or component which in turn is affixed, or connected, to the second member or component. The joined condition between the first member, or component, and the second member, or component, is intended to remain for the life of the sanitary napkin 20. Conversely, components are considered "removably affixed" if the components may be detached and separated from each other without destruction or unintended gross deformation of either.

Any joined arrangement that provides for capture of the core 26 intermediate the topsheet 22 and the backsheet 24 and a unitary assembly is suitable. Such an assembly has two mutually opposed major faces, one defined by the topsheet 22 and one defined by the backsheet 24.

The outwardly oriented face of the backsheet 24 may further comprise means 42 for attaching the sanitary napkin 20 to the undergarment of the wearer. Pressure sensitive adhesive 42 has been commonly found to work well for this purpose. Preferably a strip of longitudinally oriented adhesive 42 provides good protection against either the front or the back of the sanitary napkin 20 becoming detached from the wearer's undergarment. The adhesive strip 42 may be continuous or intermittent. A particularly preferred arrangement utilizes two longitudinally oriented strips 42, one on each side of the longitudinal centerline 34. Of course, any of the alternative means of attachment discussed above may also be utilized. Any of the desired means such as adhesive 42 may be applied in any desired pattern.

The absorbent core 26 is the means for collecting and containing bodily discharges, particularly menses, deposited thereon or which otherwise traverses through the liquid permeable topsheet 22. The core 26 is the component of the sanitary napkin 20 which receives and retains the bodily discharges. The core 26 is conformable and nonirritating to the skin. The core 26 may be rectangular or hourglass shaped. The core 26 preferably has two opposed faces, one oriented towards the backsheet 24 and one oriented towards the topsheet 22.

Suitable materials for the core 26 include combinations of airfelt, such as cellulose wadding, and fibrated communition pulp; layers of tissue paper; and absorbent gelling materials. If a tissue paper core 26 is selected, tissue paper made in accordance with U.S. Pat. No. 4,191,609 issued Mar. 4, 1980 to Trokhan and incorporated herein by reference to show a particularly preferred tissue paper core construction for the sanitary napkin 20 described herein. If it is desired to incorporate absorbent gelling materials into the core 26 of the sanitary napkin 20, absorbent gelling materials made in accordance with U.S. Pat. Re. No. 32,649 issued Apr. 19, 1988 to Brandt et al., and incorporated herein by reference for showing particularly preferred absorbent gelling materials, are suitable. A suitable laminate of absorbent gelling materials and tissue may be purchased from the Grain Processing Corporation of Muscatine, Iowa under Model Number L535.

The core 26 need not have a total absorbent capacity much greater than the total amount of bodily discharges to be absorbed. The core 26 is preferably narrow and thin, to be comfortable to the wearer. For the embodiment described herein the capacity of the core 26 should be at least about 2 grams of 0.9 percent saline solution. Suitable saline solution is sold by Travenol Laboratories of Deerfield, Ill.

The core 26 should be sized to register with the topsheet 22 and backsheet 24. The core 26 is preferably interposed between the topsheet 22 and backsheet 24 to prevent the absorbent material of the core 26 from shredding or becoming detached while the sanitary napkin 20 is worn and to ensure proper containment of bodily discharges. This arrangement also helps to provide for a unitary assembly. The sanitary napkin 20 preferably has a caliper of less than about 4 millimeters and more preferably less than about 2 millimeters, as measured with a comparator gage having an approximately 80.0 gram test weight, an approximately 10.0 gram comparator foot having a diameter of about 2.54 centimeters and a contact surface area of approximately 5.1 square centimeters. Also, the sanitary napkin 20 of the present invention should have a topsheet 22 surface area of at least about 100 square centimeters to prevent discharged fluids from missing the target area.

The core 26 is preferentially joined to the topsheet 22, and may be joined to the backsheet 24. Joining is preferentially accomplished by adhesive bonding the core 26 to the topsheet 22 or the backsheet 24. Such adhesive (not shown) may be applied in any suitable spray pattern, such as a spiral or longitudinally oriented beads. The adhesive should be surfactant resistant and of low pressure sensitivity, so as not to stick to the skin of the wearer.

The sanitary napkin 20 also comprises a flap 28 extending from a longitudinal side margin 30 of the sanitary napkin 20, and preferably one flap 28 extending from each longitudinal side margin 30 of the sanitary napkin 20. The flaps 28 have a proximal end 36 which is typically coincident with the juncture of attachment of the flap 28 to the longitudinal side margin 30 of the sanitary napkin 20 or, alternatively, the proximal end 36 of the flap 28 may be joined to the sanitary napkin 20 at any other location juxtaposed with the longitudinal side margin 30. The flaps 28 extend laterally outwardly from the sanitary napkin 20 and terminate at a distal end 38 which represents the point of the flap 28 furthest from the longitudinal axis 34 of the sanitary napkin 20. The flaps 28 maybe of any shape desired, with one preferred shape being shown in FIG. 1.

The flaps 28 are laterally outboard of the longitudinal centerline 34 and central portion of the sanitary napkin 20. As used herein the phrase "central portion" refers to that part of the sanitary napkin 20 intermediate, particularly laterally intermediate, and defined by the proximal ends 36 of the flaps 28.

The flaps 28 may be comprised of an integral and contiguous extension of the topsheet 22, the backsheet 24,or a laminate of both. Alternatively, the flaps 28 may be made of a separate and independent piece of material joined to the longitudinal side margin 30 of the sanitary napkin 20. Each flap 28 has one face generally coextensive of the topsheet 22 and a mutually opposed face generally coextensive of the backsheet 24. Faces are considered to be coextensive of the topsheet 22 or backsheet 24 if a line having a lateral component can be drawn from the central portion of the topsheet 22 or the backsheet 24 respectively, crosses a side margin 30 at the perimeter of the sanitary napkin 20, and intercepts such face.

The flaps 28 preferably have a means 40 for attaching one face of the flap 28 to the wearer's undergarment or to the other flap 28. The attachment means may be pressure sensitive adhesive 40. Any of the attachment mechanisms described above as suitable for the attachment means of the sanitary napkin 20 are also suitable for the flaps 28. Such means include the attachment mechanisms described in U.S. Pat. Nos. 5,662,758 and 6,099,940.

If pressure sensitive adhesive 40 is selected, it should be disposed on the face of the flap 28 generally coextensive of the backsheet 24 so that when the flaps 28 are wrapped around the crotch portion of the wearer's undergarment, the adhesive 40 will contact the outside of the wearer's undergarment. A generally rectangular patch of adhesive 40 on each flap 28, about 25 millimeters×20 millimeters in size works well. Any other pattern is also suitable for the adhesive pattern on the flaps 28. For example, stripes or other intermittent patterns of adhesive are suitable. There may be a gap between the attachment means on the flaps 28 and any which may be provided on the backsheet 24 of the main body portion of the sanitary napkin 20. Alternatively, such attachment mechanism (such as an adhesive) may be continuous from the flaps to the backsheet of the main body portion without a gap. Suitable pressure sensitive adhesive 40 is sold by the Anchor Continental, Inc., 3 Sigma Division of Covington, Ohio as 0.02 millimeter pass with Century Adhesive A305-4.

For packaging, including shipment and sale, the flaps 28 are folded over the topsheet 22 so that the flaps 28 are in a disposition having the topsheet facing relationship of FIGS. 1–5. The flaps 28 are considered to be in a topsheet facing relationship if a line generally perpendicular to the plane of the sanitary napkin 20 is drawn outwardly from the topsheet 22 and intercepts either face of the flap 28. The flaps 28 are preferably folded about the longitudinal lines generally coincident the proximal edges 36 of the flaps 28, so that the maximum area of the topsheet 22 may be covered by the flaps 28. This provides a larger area of the topsheet 22 which is protectively overlaid by the flaps 28, and particularly the area of the topsheet 22 which is generally registered with the wearer's vagina, so that a sanitary and clean appearance and condition of the topsheet 22 is maintained. It is not necessary that the flaps 28 be folded about the line generally coincident the proximal edge 36, that the flaps 28 be in contacting relationship with the topsheet 22, or that no other folds between the distal and proximal ends 36 and 38 of the flaps 28 occur. It is only necessary that the flaps 28 face towards and cover the topsheet 22, help prevent outside contamination from readily soiling the portion of the topsheet 22 covered by the flaps 28 and the flaps 28 are manipulable to be readily unfolded by the wearer as the sanitary napkin 20 is installed in her undergarment.

Folding the flaps 28 in the configuration of FIG. 1 exposes the patch 40 of adhesive on the face of the flaps 28 generally coextensive of the backsheet 24. To prevent contamination and blocking of this patch 40, the adhesive patch 40 of each flap 28 may be covered with a separate and dedicated piece of release strip 46.

The various embodiments of release strips 46 described herein may be advantageously made of kraft paper, calendared paper, or any other materials well known in the art for such purpose. Machine glazed or machine finished paper having a basis weight of about $40.7 \times 10^3$ kilograms per square meter (25 pounds/3,000 square feet) works well. However, the invention disclosed and claimed herein is by no means limited to any particular material selection.

Preferably the face of the release strip 46 which contacts the adhesive patches 40 has a release coating, such as silicone, to easily facilitate the removal of the release strip 46 from the flaps 28. Suitable release coatings are marketed by Akrosil of Menasha, Wis. as Silox 4R/0 and as Silox C1S.

Furthermore, the sanitary napkin 20 is preferably provided with a means for maintaining the flaps 28 in the topsheet facing relationship of FIG. 1 during packaging and prior to first use by the wearer. As used herein the "first use by the wearer" refers to the initial installation of the sanitary napkin 20 into the undergarment, so that the sanitary napkin 20 may begin to perform the intended function of collecting vaginal discharges.

One suitable means (not shown) for maintaining the topsheet facing relationship comprises a small patch of adhesive disposed on the face of each flap 28 generally co-extensive of the topsheet 22. By contacting this face of the flap 28 against the topsheet 22, the adhesive will adhere the flap 28 to the outwardly oriented face of the topsheet 22 until the flap 28 is detached by the wearer or premature, undesired separation occurs. Any adhesive FDA approved for contact with human skin is suitable. The adhesive may be either hot melt or preferably water based latex. Suitable adhesives are sold by the Findley Adhesives Company of Columbus, Ohio under the Model Nos. L8082-02 and H2128-01.

Figure 2:
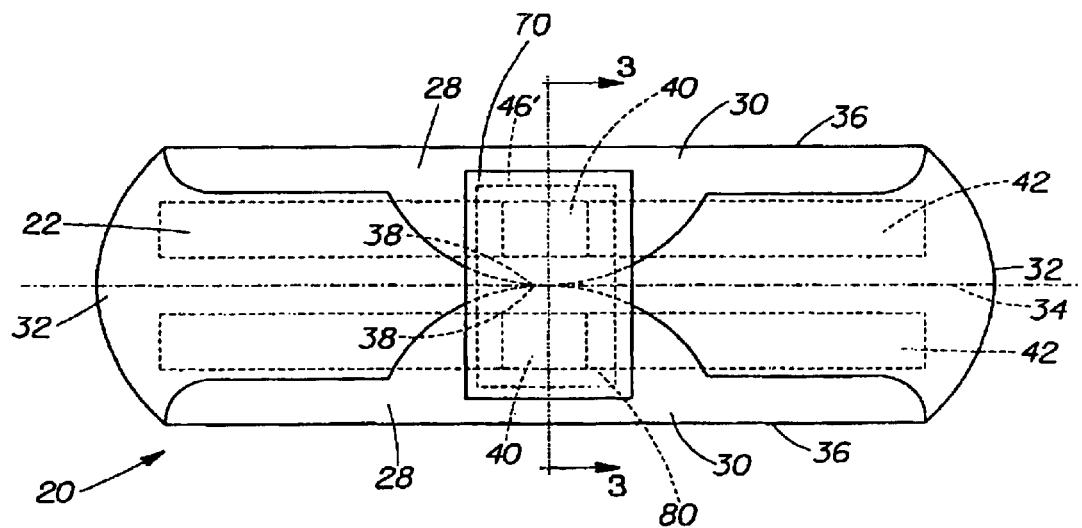
FIG. 2 is a top plan view of a sanitary napkin according to the present invention having a unitary release strip bridging the flaps.

Referring to FIG. 2, a more preferred means for maintaining the flaps 28 in the topsheet facing relationship is a unitary release strip 46' adhered to each patch 40 of adhesive on the flaps 28 and bridging both flaps 28. A component, such as a release strip 46', is considered "unitary" if it cannot be divided or disassembled without tearing or unintended gross separation. It is not necessary that a unitary component be made of a single material but, rather that such component cannot disassembled from and subsequently reassembled into the original configuration. Components are considered to be "bridged" if they do not overlap and are connectively spanned by an independent component.

This unitary arrangement provides the advantage that the flaps 28 cannot be unfolded from the topsheet-facing relationship without detaching the unitary release strip 46' and, concomitantly advantageously, the adhesive patches 40 of the flaps 28 are covered.

Preferably, but not necessarily, the release strip 46', or at least the portion of the release strip 46' which bridges the flaps 28, is longitudinally bounded by the flaps 28. As used herein, a component or portion thereof is considered to be "longitudinally bounded" by the flaps 28 if such component or portion does not extend longitudinally outboard, i.e., away from the lateral centerline, of the flaps 28. By being longitudinally bounded by the flaps 28, the release strip 46' is prevented from having substantial contact with the topsheet 22 where adhesive attachment means are typically not disposed, and an economically advantageous conservation of material occurs.

It is important that the release strip 46' be conveniently and easily manipulated by the wearer. This is because the sanitary napkin 20 is frequently attached to the crotch of the wearer's undergarment when the release strip 46' is to be removed. With a sanitary napkin 20 having a unitary release strip 46' according to this invention, the wearer can see the flaps 28 in the advantageous topsheet facing relationship of FIGS. 1 and 2, can see the release strip 46' while it is being removed and can further see the flaps 28 and adhesive patches 40 thereon while they are being manipulated into the wearing arrangement to which the wearer is accustomed. The wearer attaches the central adhesive 42 to the crotch of her undergarment, peels off the release strip 46', typically starting at either lateral edge, folds the flaps 28 around the edges of the crotch of the undergarment, and attaches the flaps 28 to the outside of the undergarment using the flap adhesive 40.

The sanitary napkin 20 of the present invention is packaged with a wipe article, preferably a cleansing wipe 80. According to the present invention, the wipe article is associated with the means for maintaining the flaps in a topsheet facing relationship. In this manner, as shown below, the wipe article is provided with minimal additional material components, and with virtually no inconvenience to the user.

The cleansing wipe 80 is a hygienic wipe that may be used by the wearer to clean menses and/or other body exudates from her body. The cleaning of menses is particularly important because when menses leaves the wearer's body, it tends to smear over the pudendal region of the wearer's body and be retained on the wearer's skin and pubic hair. Furthermore, the menses often dries on the skin and in the pubic hair. This makes later cleansing difficult.

The cleansing wipe 80 of the present invention is beneficially associated with the means for means for maintaining the flaps 28 in the topsheet facing relationship. In one embodiment, the wipe 80 is enclosed in a pouch 70, a portion of which comprises the unitary release strip 46'. In another embodiment, the wipe pouch itself, whether or not considered to by "unitary" also serves as the release strip.

The convenient inclusion of a cleansing wipe with the individual sanitary napkin in the manner described herein provides several advantages. The wipe 80 of the present invention is provided in such a way as to minimize the amount of extra material required to product the sanitary napkin/wipe combination. A portion of the wipe pouch, as more fully described below, can serve as the means for maintaining the flaps 28 in the topsheet facing relationship (i.e., a portion thereof also being the release strip) thereby minimizing additional material components to the sanitary napkin product. Also, due to the placement of the wipe and its containment pouch, the user does little different in the way of installing the sanitary napkin, whether or not the user actually uses the wipe. In fact, the user may choose not to use the wipe, and does nothing different in otherwise using the sanitary napkin. That is, as shown below, the wipe packaging, i.e., pouch 70, can be simply removed as the release strip 46' would otherwise be removed.

The wipe 80 provides for physical cleansing. This increases physical comfort as well as psychological comfort by providing a feeling of cleanliness. The wipe may also be used to reduce soiling of the wearer's panties. One mechanism that causes panty soiling is the transfer of menses from soiled body surfaces to the wearer's panties. In addition, the use of the wipe may also provide a reduction in the odor associated with menstruation.

The cleansing wipe 80 is preferably a wet wipe (that is, liquid containing) that is provided with an aqueous-based solution. The wipe 80 is preferably comprised of a nonwoven fabric impregnated with an aqueous cleaning mixture. The nonwoven fabric may be comprised of synthetic fibers or natural fibers (such as cellulose). The wipe 80 can, for instance, be made of a nonwoven material similar to toilet tissue or facial tissue. Less preferred embodiments might include dry wipes or wipes containing non-aqueous cleaning solutions such as mineral oils, and the emollient described in U.S. Pat. No. 4,481,243, issued to Allen on Nov. 6, 1984. The cleaning mixture may include surfactants, alcohols, perfumes, antimicrobial agents, and pH buffers.

The wipe 80 may also contain substances such as silicones that tend to inhibit menses from adhering to the wearer's skin and pubic hair. The cleaning mixture may also contain skin conditioning substances similar to those used in hand lotions, or any other substances known in the art for inclusion in cleansing wipes. The cleansing wipe 80 is preferably both capable of being flushed in a toilet (i.e., it is "flushable"), and disintegrates sufficiently when flushed in a toilet and when being transported in the sewer system so it does not plug any element of a sewer system.

In preferred embodiments, any wrapping material associated with the wipe is also flushable and disintegrates. Wrapping materials that meet such criteria include, but are not limited to silicone-treated polyvinyl alcohol films, or films coated with a polyvinyl alcohol, tissue coated or impregnated with polyvinyl alcohol, or similar or other water soluble materials. One material that may be suitable for use as both a cleansing wipe, and as a wrapping for the same is the hydro-entangled fabric described in U.S. Pat. No. 4,755,421, issued to Manning, et al. on Jul. 5, 1988.

The size of the cleansing wipe 80 can vary. The cleansing wipe 80 is preferably greater than or equal to about 4 square inches (about 25 square centimeters), and more preferably, is greater than or equal to about 9 square inches (about 50 square centimeters) in size. Preferably, the cleansing wipe 80 is less than or equal to about 225 square inches (about 1,450 square centimeters) in size. Even more preferably, the cleansing wipe 80 is between about 16 square inches (about 100 square centimeters) and about 50 square inches (about 320 square centimeters) in size. Most preferably, the wipe 80 is about 35 square inches (about 225 square centimeters) in size. The wipe is folded in any known and convenient manner desired to be disposed in the pouch 70 as described below.

The wipe 80 is packaged in a manner that is convenient for the wearer to use during the installation of a sanitary napkin in her undergarment. That is, to access and use the wipe of the present invention requires little more effort than is already being expended by the user. This is important because the user is often concerned with speed, ease of use, and discreteness during the changing of a sanitary napkin. For example, the user may be in a location, such as a public restroom stall, that makes movement difficult, particularly while trying to maintain cleanliness. At these times, the user does not want to have to manage complicated or inconvenient steps to access or use a wipe product while at the same time installing a sanitary napkin.

Therefore, to use a sanitary napkin of the present invention, the user would typically remove release strip 43 (or release liner 48 in the alternative embodiment described below with reference to FIGS. 6–9) and attach central adhesive 42 to the crotch of her undergarment. She would then remove pouch 70 with or without also removing release liner 46'. Depending on the particular configuration, as described herein, the release liner may or may not be an element wholly separate from pouch 70. The user now folds the flaps around the side edges of the crotch portion of her undergarment, and, if adhesive means are present, attaches flaps to the underside of her undergarment. She then, if desired, uses the wipe provided by opening the pouch, using the wipe, and disposing of the wipe and package appropriately.

In this manner, it is evident that the user does little different from the ordinary routine of placing a sanitary napkin in her undergarment. She does not have to manipulate a wipe article from an unassociated, separate package. Moreover, she does not have to make any extra effort to remove an unwanted wipe, since she would be removing the release strip anyway.

The drawing figures show several nonlimiting alternative ways of associating the wipe article with the means for maintaining said flaps in a topsheet facing relationship.

Figure 3:
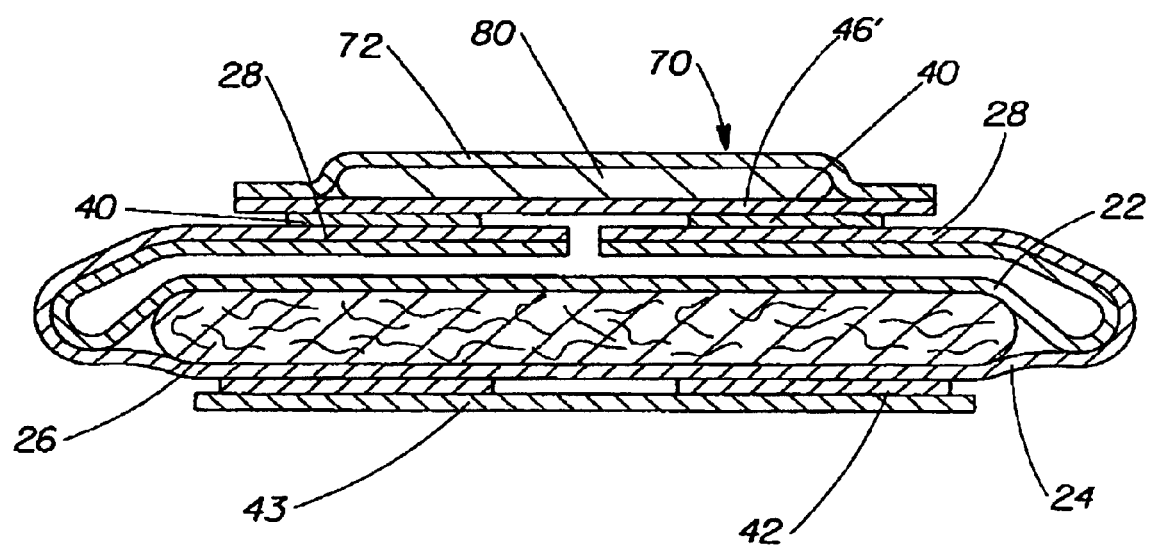
FIG. 3 is a cross-sectional view of section 3—3 of the sanitary napkin of FIG. 2.

One embodiment of the present invention is shown in FIG. 3, which is a cross-section of the sanitary napkin of FIG. 2. In this embodiment, wipe 80 is packaged in a pouch 70, which is preferably hermetically sealed by known methods. Pouch 70 is formed by sealing the edges of a pouch cover 72 to the release strip 46' to define a containment space in which the wipe 80 is disposed. Thus, in this embodiment, the pouch 70 comprises the release strip 46'.

The pouch cover 72 can be made of any suitable material, such as polymer films, film laminates, paper, or nonwovens, and, as discussed above, is preferably flushable. If the wipe 80 is a wet wipe, i.e., a pre-moistened wipe, the pouch cover 72 (and pouch 70) must be liquid impervious. The wipe may be a dry wipe, in which case the pouch cover can be made of a fluid pervious material such as a soft, pliable nonwoven web material.

The pouch cover 72 can be joined to the release strip 46' in any suitable manner, such as by adhesive, thermal bonding, or ultrasonic bonding. The pouch cover 72 and release strip 46' can be made into pouch 70 in a separate unit operation and subsequently attached by known methods as a release strip to sanitary napkin 20. However, the wipe 80 and pouch cover 72 (or pouch 70 as disclosed below) may be added by known methods in a separate manufacturing step after the release strip 46' is placed on sanitary napkin 20. In one less preferred embodiment, the pouch 70 could be adhesively affixed by hand to a sanitary napkin.

Pouch cover 72 can be provided with a grip tab (not shown) to aid in gripping the cover for removal. In use, the user may remove pouch cover 72, use or remove the wipe, and then remove release strip 46'. Alternatively, the user may choose to first remove the pouch 70 entirely, including the release strip 46', then open the pouch by separating the pouch cover 72 from the release strip 46'.

Figure 4:
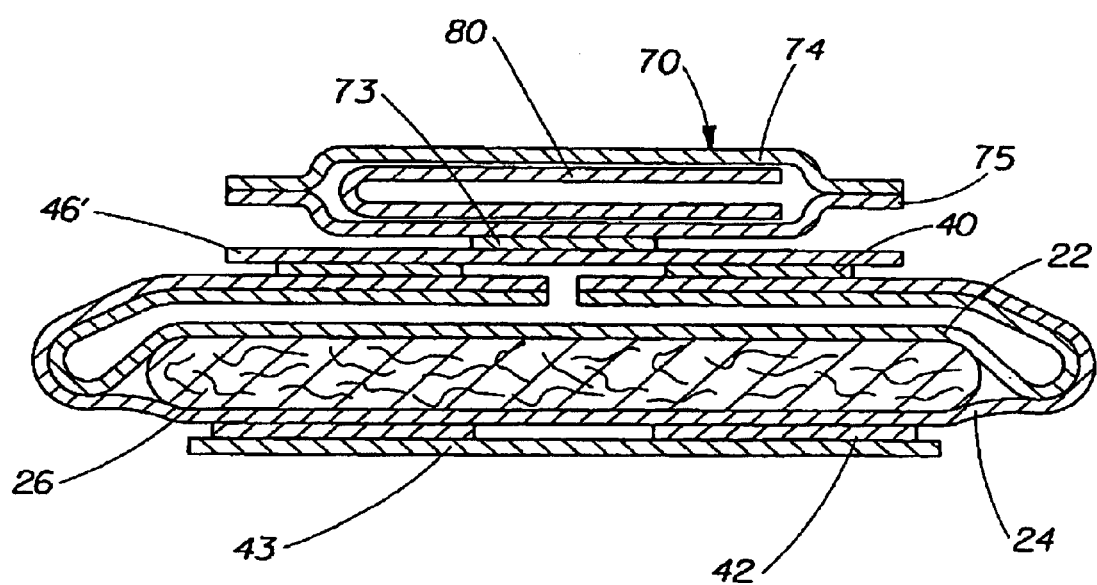
FIG. 4 is a cross-sectional view of another embodiment of a sanitary napkin of the present invention.

In another embodiment shown in FIG. 4, the pouch 70 is formed of a first pouch material 74 and a second pouch material 75 which preferably have substantially the same dimensions and are joined about their respective peripheral edges by suitable methods, such as by adhesive bonding. The pouch 70 is joined by suitable methods, such as by adhesive 73 to the release strip 46'. The first and second pouch materials 74, 75 may be identical. For example they may both be a polymer film, a metal foil, or a metalized polymer film. Likewise, they may be a soft, pliable nonwoven, or a nonwoven/film laminate. The first and second pouch materials may be different materials, but in any combination it is necessary that they be joinable about their respective peripheries, preferably to form a hermetic seal.

In the embodiment disclosed in FIG. 4, it is not necessary that the pouch 70 be easily removable from release strip 46'. In use, the user would remove the pouch 70, which could then beneficially affect removal of the release strip 46'. The user could then, if desired, open pouch 70 with release strip still joined. The user could then simply dispose of pouch 70 and release strip 46' as a unit. However, in another embodiment, the joining means, such as adhesive 73 between pouch 70 and release strip 46' can have less peel strength than that of the adhesive between release strip 46' and backsheet 24, such that the user could easily first remove pouch 70, use the enclosed wipe 80, and then remove release strip 46'.

In any of the embodiments, the pouch 70 configuration may be any desired shape. For example, the pouch 70 may be a square, rectangle, oval, circle, or any other desired shape in plan view. The pouch may be a simple "wrapper" type design, or could have an opening which is covered with a cover attached with adhesive. One execution may include a wrapper with a scored or die cut line of weakness in the top surface of the pouch 70, this line of weakness may allow the pouch 70 to be opened easily with a tab, easy peel label or any other conventional opening mechanism. A "Dry-edge" sticker mechanism may also be used to facilitate easy opening of the pouch 70 if desired.

Figure 5:
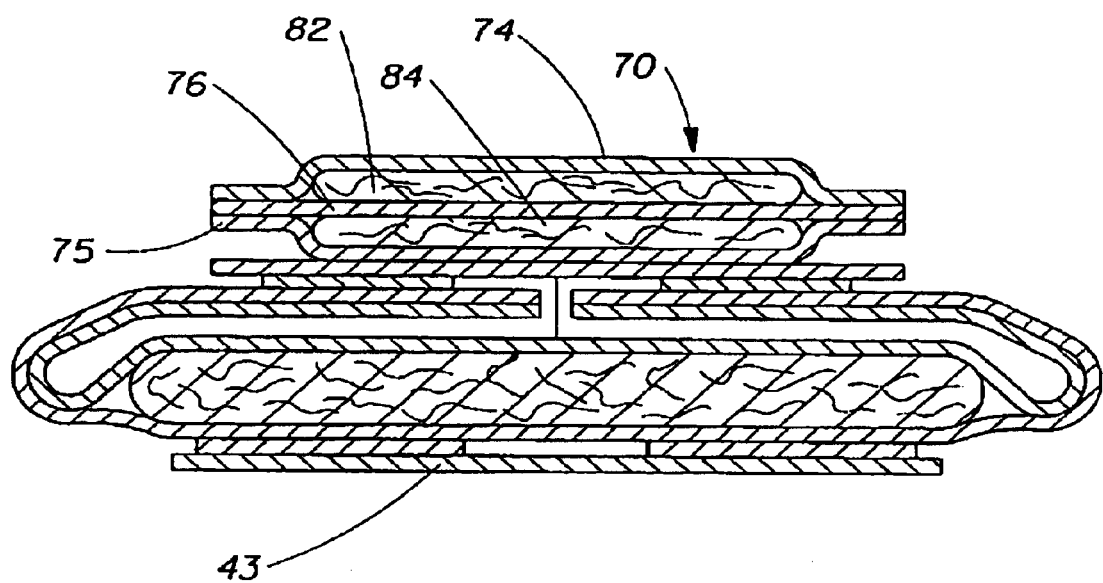
FIG. 5 is a cross-sectional view of another embodiment of a sanitary napkin of the present invention.

In another embodiment shown in FIG. 5, the pouch 70 is formed having two discrete containment spaces, each having a wipe 80 contained therein. In this embodiment, the pouch 70 is formed from three materials: a first pouch material 74; as second pouch material 75, and a third pouch material 76 disposed between the first and second pouch materials. Each of the first, second and third pouch materials can have similar dimensions and can be joined about their respective peripheral edges. As shown in FIG. 5, such an arrangement forms a pouch having two compartments, or containment spaces, into which a wipe 80 can be disposed. In a preferred embodiment, the region bounded by first pouch material 74 and third pouch material 76 comprises a wet wipe 82, and the region bounded by the third pouch material 76 and the second pouch material 75 comprises a dry wipe 84. In use, the user can first access and use the wet wipe 82, and thereafter, if desired, access and use the dry wipe 84 provided.

As discussed above, for each embodiment wherein the pouch 70 does not comprise a portion of release tape 46', it is not critical whether or not the user first removes the pouch

70 and then the release tape 46', or removes the release tape 46' together with the pouch 70.

In one embodiment, it may be desirable to eliminate the attachment means 46 associated with the flaps 28. That is, in certain less preferred embodiments, a sanitary napkin may have flaps 28 with no attachment adhesive on the flaps for attaching to the wearer's undergarments. Nevertheless, the benefits of the present invention can be realized by packaging the sanitary wipe with the flaps 28 folded in a topsheet facing relationship, and providing a wipe article as discussed above. In this configuration, the pouch 70 would be affixed by suitable means, including autogenously, to flaps 28. By "autogenously" means without the benefit of external means such as adhesives and the like. One example of autogenously bonding is exhibited when two nonwoven webs are pressed together such that a certain amount of fiber entanglement between the two facilitates a light bond. In a preferred execution of this embodiment, pouch 70 would be releasably affixed to flaps 28. As used herein, "releasably affixed" refers to the condition of two or more components which may be attached and separated without destruction of or undue distortion to either component. For example, pouch 70 can be affixed by a relatively small amount of adhesive which permits the pouch to be removed without damaging the flap material.

Therefore, in one embodiment, the invention can be described as a sanitary napkin having a pair of flaps, each flap extending from a longitudinal side margin of the sanitary napkin, and means for maintaining the flaps in a topsheet facing relationship, the means having a wipe article associated therewith. The flaps preferably have attachment means associated with a garment facing portion. The means for maintaining the flaps in a topsheet facing relationship preferably comprises a release strip that bridges at least the distal ends of the flaps. The wipe article is preferably comprises an enclosed pouch, with the wipe article disposed therein. The wipe article can be a wet wipe or a dry wipe.

The sanitary napkin of the present invention having a wipe article associated therewith may be provided as an individually wrapped absorbent article. In general such articles are described in U.S. Pat. No. 4,462,166, issued Oct. 31, 1995 to Minton et al., which is hereby incorporated herein by reference, and as well in the aforementioned U.S. Pat. No. 5,569,230 issued Oct. 29, 1996 to Fisher et al. Particular embodiments are described below with reference to FIGS. 6–8.

Figure 6:
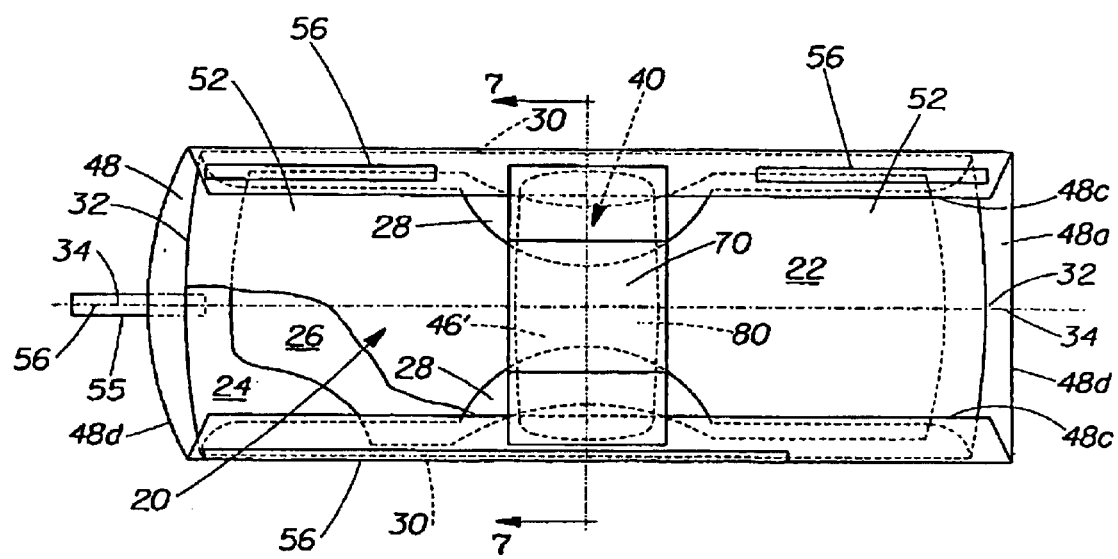
FIG. 6 is a top plan view, shown partially in cutaway, of another embodiment of a sanitary napkin according to the present invention.

As shown in FIG. 6, the sanitary napkin 20 is superimposed on a releasable wrapper (or "release paper wrap") 48. (The releasable wrapper need not be paper, however.) The releasable wrapper 48 underlays and is releasably affixed to the outwardly oriented face of the backsheet 24. In the embodiment shown, the releasable wrapper 48 is slightly larger than the central portion of the sanitary napkin 20 as it is defined by the longitudinal and lateral side margins 30 and 32.

The releasable wrapper 48 contacts the adhesive 42 of the backsheet 24, and if desired, the adhesive 40 of the flaps 28, to help prevent contamination of such adhesive 40 prior to first use by the wearer. Also, the releasable wrapper 48 prevents the otherwise exposed adhesive 42 from sticking to other parts of the sanitary napkin 20 when the napkin is inwardly trifolded.

The releasable wrapper 48 has a perimeter defined by longitudinal edges 48c and lateral edges 48d. Preferably, the lateral edges of the releasable wrapper 48 are juxtaposed with the respective lateral side margins 30 of the sanitary napkin 20. This arrangement provides a releasable wrapper 48 having sufficient longitudinal extent to conceal and to protect the sanitary napkin 20 in the later described folded configurations.

The wrapper 48 has opposed faces. One face is an inwardly oriented face 48a. The inwardly oriented face of the wrapper 48 is oriented towards the adhesive 42 and the outwardly oriented face of the backsheet 24. The other face 48b is an outwardly oriented face. It is opposed to the inwardly oriented face and oriented away from the sanitary napkin 20.

Preferably, the inwardly oriented face is release coated, to facilitate easy and convenient manipulation of the releasable wrapper 48, and particularly separation from the adhesive 40 and 42. Silicone release coatings, as are well known in the art, have been found to work well. The releasable wrapper 48 may be zone coated with the release coating only in the areas of the adhesive 40 and 42, or may be entirely release coated throughout the inwardly oriented face as desired. The releasable wrapper 48 may be made of films, kraft paper, calendared paper, or other materials as are well known in the art without departure from the spirit and scope of the claimed invention.

One suitable releasable wrapper 48 is made of machine glazed or machine finished paper having a basis weight of about $40.7 \times 10^3$ kilograms per square meter (25 pounds per 3,000 square feet). The inwardly oriented face of the wrapper may be coated with a release coating such as silicone. Suitable release coated wrapper materials are marketed by Akrosilof Menasha, Wis. as Silox 4R/O and Silox C1S.

The releasable wrapper 48 may be made of one or more sheets of material. The wrapper 48 may, for instance, comprise a two component arrangement comprising the wrapper 48 as described herein that is combined with a conventional release strip that covers the adhesive 42 attached to the inwardly oriented face of the wrapper 48. Preferably, however, the releasable wrapper 48 comprises a single sheet that both covers the adhesive 42 and serves as a package for the sanitary napkin 20.

Figure 7:
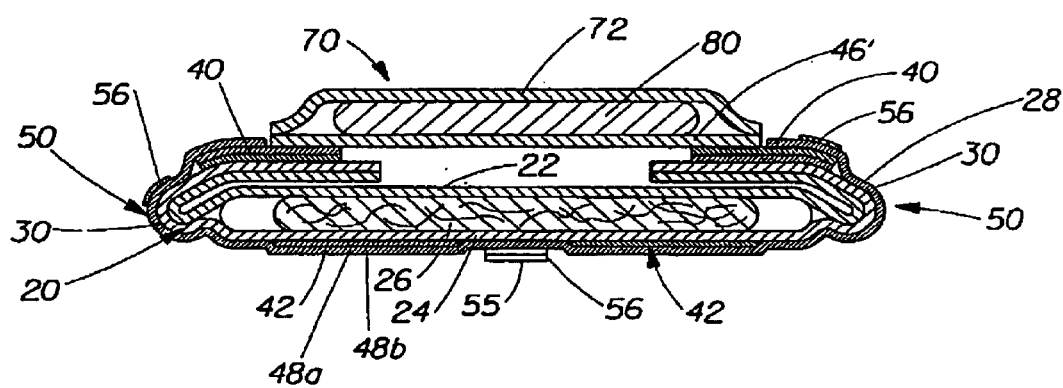
FIG. 7 is a cross-sectional view of section 7—7 of the sanitary napkin of FIG. 6.

With continuing reference to FIG. 7, it can be seen that in one embodiment, the releasable wrapper 48 wraps at least one, and preferably each, longitudinal side margin 30 of the sanitary napkin 20 in a C-fold 50. As used herein, a "C-fold" refers to the configuration of a component which is folded over itself to provide a double thickness and may have a foreign component interposed between the layers of the folded component.

As illustrated in FIG. 7, it is preferred that the sanitary napkin 20 and releasable wrapper 48 be equivalently and symmetrically disposed and folded about the longitudinal centerline 34. In the C-folded arrangement of FIG. 7, the entire backsheet 24 is covered by the releasable wrapper 48 and a portion of the topsheet 22 juxtaposed with the longitudinal side margins 30 are also covered by the releasable wrapper 48.

As used herein, "releasable" refers to the condition where a first component may be separated from a second component at least once without causing destruction or undue distortion of either component. The illustrated arrangement provides the advantage that one entire major face, particularly the face associated with the backsheet 24, is protected by the releasable wrapper 48. The longitudinal side margins 30 of the sanitary napkin 20 are likewise protected. Additionally, a portion of the topsheet 22 is protected by the releasable wrapper 48. Further, in this arrangement no significant portion of the releasable wrapper 48 extends laterally outboard of the sanitary napkin 20, obviating the need for a bulky package, or a region of the releasable wrapper 48 to be dedicated for sealing of the package.

Figure 8:
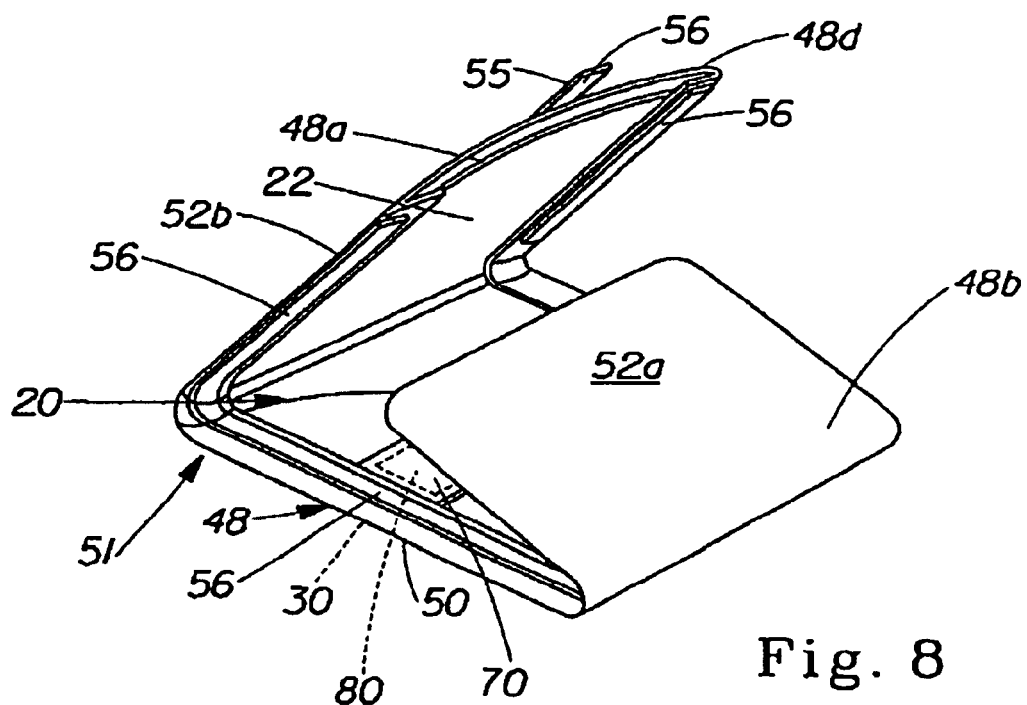
FIG. 8 is a perspective view of an embodiment of the present invention in a partially folded configuration.

As illustrated in FIG. 8, the sanitary napkin 20 and releasable wrapper 48 may be folded about two spaced-apart laterally oriented fold lines. As used herein, the phrase "spaced-apart laterally oriented fold lines" refers to longitudinally offset lines, generally parallel the lateral direction, and about which the sanitary napkin 20 and releasable wrapper 48 are commonly folded.

Folding the sanitary napkin 20 about the spaced apart laterally oriented fold lines produces a folded arrangement defining three trisections 51 and 52, a central tri-section 51 intermediate and bounded by two outboard trisections 52. The outboard trisections 52 may be more specifically described as an inner-outboard trisection 52a and an outer-outboard trisection 52b, or more simply as the first and third trisections.

The central trisection 51, thus comprises the second trisection. As used herein, inner and outer outboard trisections 52 are described relative to the central trisection 51 when the sanitary napkin 20 and releasable wrapper 48 are in the folded arrangement of FIG. 9. The inner-outboard trisection 52a is generally adjacent the central trisection 51 and intermediate such central trisection 51 and the outer-out-board trisection 52b when folded. Conversely, the outer-outboard trisection 52b is relatively further from the central trisection 51 due to the interposition of inner-out-board trisection 52a.

Figure 9:
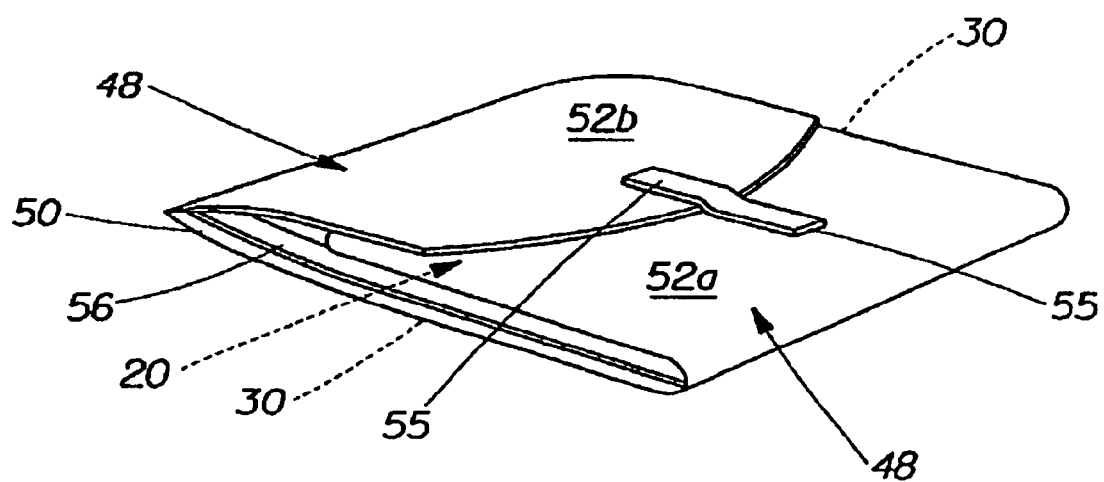
FIG. 9 is an perspective view of one embodiment of the present invention in a fully folded configuration.

In the folded arrangement, as shown in FIG. 9, the package defines two mutually opposed major surfaces, one defined by the outer-outboard trisection 52b, and one defined by the central trisection 51. The arrangement of FIG. 9 produces a packaged sanitary napkin 20 having an e-fold with a releasable wrapper 48 having a corresponding e-fold. The releasable wrapper 48 is preferably of sufficient longitudinal dimension to overlie one outboard trisection 52 and the central trisection 51. More preferably, the releasable wrapper 48 is of sufficient longitudinal dimension to overlie all three trisections 51 and 52, so that no adhesive 40 or 42 is exposed.

Referring back to FIG. 6, the releasable wrapper 48 may further comprise a means for maintaining the sanitary napkin 20 and releasable wrapper 48 in the aforementioned folded arrangement. Suitable means for maintaining the folded arrangement include hook and loop mechanical fasteners, such as are sold under the trademark VELCRO mechanical fasteners; heat and/or pressure seals; and, adhesives in the form of tabs, or adhesive 56 juxtaposed with the longitudinal edge of the releasable wrapper 48. The adhesive 56 may be placed on the longitudinal edge of the releasable wrapper which is folded over so that it overlays and faces outwardly from the topsheet 22. In one execution, the adhesive 56 may be applied to the outboard trisections 52 so that when the inner-out-board trisection 52a is folded over the central trisection 51 such trisections 51 and 52a are releasably affixed to each other and adhesive is juxtaposed with the outer-out-board trisection 52b so that it may be releasably affixed to the inner-outboard trisection 52a.

Alternatively, the adhesive 56 may be applied to the central and outer-out-board trisections 51 and 52b. The adhesive 56 may be applied in a continuous strip (as shown), in an intermittent strip, or may be a single spot. It is not critical which form the adhesive 56 is applied, only that it have sufficient peel strength to maintain the folded arrangement until it is desired to conveniently open the sanitary napkin 20 and releasable wrapper 56 for the first use by the wearer.

In one variation, the adhesive 56 may further comprise and be disposed on a tab 55 longitudinally extending beyond the lateral edge of the outer-outboard trisection 52b. The adhesive 56 of the tab 55 longitudinally beyond such lateral edge is affixed to the exposed face of the inner-outboard trisection 52a.

As with the sanitary napkin described with reference to FIGS. 1–5, the individually wrapped absorbent article described also has a wipe article associated therewith, disposed in pouch 70 which is joined to, or at least partially serves as, release strip 46'. The embodiment shown in cross-section in FIG. 7, for example, corresponds to the embodiment shown in FIG. 3. Without repeating the description provided above, the individually wrapped embodiment of the present invention can have the same pouch and wipe article configurations as the embodiments described with reference to FIGS. 3–5.

As shown in FIG. 7, release paper 46' bridges at least the distal ends of wings 28 and partially covers the wing adhesive 40. However, the release paper does not extend onto, or cover any portion of releasable wrapper 48. Therefore, releasable wrapper 48 can be unfolded and removed without disturbing the release paper 46' or the wipe article associated therewith. In use, therefore, the wearer can remove releasable wrapper 48, place the sanitary napkin in the crotch portion of her undergarment, and then proceed to remove the release liner and/or the wipe article.

The wipe article for the individually wrapped embodiment of the present invention preferably comprises cleansing wipe 80 as described above. Likewise, the pouch 70 comprises materials and configurations as described above. Moreover, as described above with respect to the sanitary napkin of FIGS. 1–5, in a less preferred embodiment, the wing adhesive 40 of the individually wrapped embodiment may be omitted.

Thus, in one embodiment, the invention can be conveniently described as an individually packaged sanitary napkin having a pair of flaps folded and maintained in a topsheet facing relationship by means having a wipe article associated therewith. A releasable wrapper serves as a release paper for an adhesive fastener disposed on the backsheet, which wrapper can be folded about the longitudinal edges of the sanitary napkin. The entire package of sanitary napkin and releasable wrapper can be tri-folded and affixed into a convenient, relatively thin, single-use package.

In any of the embodiments described above, the release means for the flaps 28 could be directly attached to the releasable wrapper 48 in any suitable configuration: Examples of such configurations are described further in U.S. Pat. No. 6,074,376.

While particular embodiments of the present invention have been illustrated and described, it would be obvious to those skilled in the art that various other changes and modifications can be made without departing from the scope of the invention. For example, various indicia, including logos, printed matter, and embossed designs could be included on the pouch 70 cover disclosed herein. Also the pouch could have mult-purpose wipes, such as a wipe for cleaning, and a wipe for fragrance, each provided in a suitably-configured pouch 70.

What is claimed is:

1. An absorbent article having a body-faceable side, a garment-faceable side, a length, a width, two longitudinal side margins, said absorbent article comprising:

a liquid pervious topsheet;

a liquid impervious backsheet joined to said topsheet;

an absorbent core positioned between said topsheet and said backsheet;

a pair of flaps, each said flap extending from a longitudinal side margin;

each of said flaps being folded over said topsheet in a topsheet facing relationship; and an enclosed pouch maintaining said flaps in said topsheet facing relationship, said enclosed pouch being releasably affixed to said flaps, said enclosed pouch having a wipe article disposed therein.

2. The absorbent article of claim 1, wherein each said flap has a garment faceable portion and attachment means disposed on said garment faceable portion.

3. The absorbent article of claim 2, wherein said attachment means comprises pressure sensitive adhesive.

4. The absorbent article of claim 1, wherein said pouch is hermetically sealed.

5. The absorbent article of claim 1, wherein said wipe article is a dry wipe.

6. An individually packaged sanitary napkin comprising:

a sanitary napkin having a body-faceable side, a garment-faceable side, a length, a width, and two longitudinal side margins, said absorbent article comprising:

a liquid pervious topsheet;

a liquid impervious backsheet joined to said topsheet, said backsheet having opposed inwardly and outwardly oriented faces;

an absorbent core positioned between said topsheet and said backsheet;

a pair of flaps, each said flap extending from a longitudinal side margin;

each of said flaps being folded over said topsheet in a topsheet facing relationship;

an enclosed pouch maintaining said flaps in said topsheet facing relationship, said enclosed pouch being releasably affixed to said flaps, said enclosed pouch having a wipe article disposed therein; and a releasable wrapper releasably affixed to an adhesive fastener on said outwardly oriented face of said backsheet, said releasable wrapper having a longitudinal dimension, a transverse dimension, and inwardly oriented face, an outwardly oriented face, a pair of longitudinal side edges, a pair of end edges, and a pair of ends, wherein only said releasable wrapper is folded about a longitudinal axis adjacent at least one of said longitudinal edges of said sanitary napkin in a C-fold thereby wrapping said at least one of said longitudinal edges, and wherein said sanitary napkin and said releasable wrapper are folded about two transverse axes which form said wrapper into first, second, and third trisections.

7. The absorbent article of claim 6, wherein each said flap has a garment faceable portion and attachment means disposed on said garment faceable portion.

8. The absorbent article of claim 7, wherein said attachment means comprises pressure sensitive adhesive.

9. The absorbent article of claim 6, wherein said pouch is hermetically sealed.

10. The absorbent article of claim 6, wherein said wipe article is a dry wipe.

\* \* \* \* \*